(12) United States Patent
Kutsch et al.

(10) Patent No.: US 9,968,526 B1
(45) Date of Patent: May 15, 2018

(54) SYSTEM FOR CARIES MANAGEMENT BY RISK ASSESSMENT

(75) Inventors: V. Kim Kutsch, Jefferson, OR (US);
Robert J. Bowers, Albany, OR (US);
Jesse L. Droesch, Albany, OR (US);
Douglas A. Young, Orinda, CA (US)

(73) Assignee: DENTAL ALLIANCE HOLDINGS, LLL, Albany, OR (US)

( * ) Notice: Subject to any disclaimer, the term of this patent is extended or adjusted under 35 U.S.C. 154(b) by 2760 days.

(21) Appl. No.: 11/337,435

(22) Filed: Jan. 23, 2006

Related U.S. Application Data

(60) Provisional application No. 60/646,246, filed on Jan. 24, 2005.

(51) Int. Cl.
*A61K 8/21* (2006.01)

(52) U.S. Cl.
CPC ...................... *A61K 8/21* (2013.01)

(58) Field of Classification Search
None
See application file for complete search history.

(56) References Cited

U.S. PATENT DOCUMENTS

| | | |
|---|---|---|
| 4,150,151 A | 4/1979 | Pader et al. |
| 4,372,978 A | 2/1983 | Gilbertson et al. |
| RE31,815 E | 1/1985 | Alfano |
| 5,213,615 A | 5/1993 | Michl |
| 5,607,672 A | 3/1997 | Hillman |
| 5,738,113 A | 4/1998 | Connelly |
| 5,770,182 A | 6/1998 | Fischer |
| 5,804,165 A | 9/1998 | Arnold |
| 6,043,047 A | 3/2000 | Foote et al. |
| 6,314,960 B1 | 11/2001 | Vines |
| 6,342,207 B1 | 1/2002 | Stoor et al. |
| 6,375,934 B1 | 4/2002 | Eklund et al. |
| 6,484,144 B2 | 11/2002 | Martin et al. |
| 6,548,018 B2 | 4/2003 | DiCesare et al. |
| 6,685,921 B2 | 2/2004 | Lawlor |
| 6,846,478 B1 | 1/2005 | Doyle et al. |
| 2002/0114768 A1 | 8/2002 | Stoor et al. |
| 2005/0025720 A1 | 2/2005 | Bailey |
| 2005/0100866 A1 | 5/2005 | Amone et al. |
| 2005/0142074 A1 | 6/2005 | Pushpangadan et al. |
| 2005/0169852 A1 | 8/2005 | Roberge et al. |
| 2005/0191247 A1 | 9/2005 | Drake et al. |
| 2008/0057531 A1 | 3/2008 | Machida et al. |

OTHER PUBLICATIONS

Featherstone et al. (J. Calif. Dental Assoc., Mar. 2003).*
Davidson et al. (Luminescence, 14:33-38, 1999).*
Robrish et al. (Appl. Environ. Microbiol., 35:743-749, 1978).*
Kutsch-Renyer Newsletter Fall/Winter 2005, Albany, OR 97321, patient newsletter. see p. 1 for relevant information.
Kutsch, VK: CAMBRA: Caries Management by Risk Assessment, Part IOregon/SW Washington Doctor of Dentistry, Jan. 2004.
Kutsch, VK: How to Integrate CAMBRA into a Dental Practice, Part II, Oregon/SW Washington Doctor of Dentistry, Feb. 2004.
Steimke, A., Dtsch. zahnarztl. Z. 38, 918-920 (1983) (Englsih abstract is on p. 920).
www.kpchr.org/public/dental/mission.htm Mission Statement, Oral Health Research Progrm (no named author).
Spaeth, Dennis, Not your father's dentistry, Dental Practice Report, Jul./Aug. 2003.
Zickert, Ingegerd et al: Effect of Caries Preventive Measures in Children Highly Infected with the Bacteium *Streptococcus mutans*, Archs Oral Biol vol. 27 pp. 861-868.
Rethman, Jill, Trends in Preventive Care Caries Risk Assessment and Indications for Sealants, JADA, vol. 131, Jun. 2000.
Search printout from Google, Feb. 21, 2004 from searching Kutsch and Chicago Midwinter (six pge search pintout, no author).

\* cited by examiner

*Primary Examiner* — Brian Gangle
(74) *Attorney, Agent, or Firm* — John J. Connors; Connors & Assoc. pc.

(57) ABSTRACT

The invention provides the tools needed for a dental patient's caries risk assessment. Included is a complete turnkey system for caries risk assessment and treatment, including an ATP test and a plurality of rinses and educational and diagnostic materials. The system for the detection and treatment of the bacterial infection that causes dental caries in a patient comprises a disposable ATP Bioluminescence sampler to swab areas of the patient's mouth, a bioluminescent light meter which measures the amount of ATP present in the patient's mouth, a rapid culture test for the detection of *Mutans* streptococci and lactobacilli, a diagnostic testing component that includes a caries risk assessment questionnaire, a treatment component that includes a short term therapeutic oral rinse of at least two components, and a long term maintenance rinse.

7 Claims, 9 Drawing Sheets

CARIES RISK ASSESSMENT FORM - ADULTS/CHILDREN AGED 6 YEARS AND OVER

Patient Name: _____ Chart # _____ Age _____
Assessment date: _____ Is this: (please circle)  Baseline  or  Recall

| FACTORS | HIGH | MODERATE | LOW |
|---|---|---|---|
| 1. Local Factors | (Please circle responses) | | |
| Plaque/Calculus | generalized | localized | minimal/none |
| 2. Dental Conditions | | | |
| *Visible cavitations | YES | | no |
| Cavity in last 3 years | yes | | no |
| +Inadequate saliva flow | yes | | no |
| Exposed roots | | yes | no |
| Deep pits/fissures | | yes | no |
| Radiographic lesions | | yes | no |
| White spot lesions | | yes | no |
| Appliances present | yes | | no |
| 3. Medical History: | | | |
| Sjogren's syndrome | yes | | no |
| Hyposalivary meds | yes | | no |
| Radiation Therapy | yes | | no |
| 4. Dietary Habits | | | |
| Snacks between meals | >3 times | 1-3 times | infrequent |
| Regular Soda | yes | infrequent | no |
| 5. Environmental | | | |
| Recreational drugs | yes | | no |
| 6. Protective Factors | | | |
| Fluoridated water | no | | yes |
| Fluoridated toothpaste | no | | yes |
| Adequate saliva flow | no | | yes |
| Fluoride mouthrinse | | no | yes |
| Xylitol gum/mints | | no | yes |
| Chlorhexidine rinse | | no | yes |
| Povidone Iodine rinse | | no | yes |
| 7. Laboratory Tests | | | |
| Saliva Flow | Recommended | Recommended | Optional |
| Bacterial Culture | Recommended | Recommended | Optional |
| Lab Test Results: MS: | LB: | Flow Rate: | ml/min. |

← 10

1    2    3    4

CARIES RISK
    ASSESSMENT:       HIGH        MODERATE        LOW
PROGNOSIS:                POOR        MODERATE        GOOD

Figure 1

Notes for Figure 9

Maxillary means top teeth (1-16)
  Maxillary right first molar is #3; second molar is #2

Premolars on the right side are numbers 4 and 5

Incisors are the four front teeth

Buccal is the outside surface of the back teeth;
Lingual is the tongue-side surface of the back teeth Mesial to distal means "front to back"

SYSTEM FOR CARIES MANAGEMENT BY RISK ASSESSMENT

RELATED PATENT APPLICATION

This utility application claims the benefit under 35 USC 119(e) of U.S. Provisional Patent Application No. 60/646,246, entitled "System for Caries Management by Risk Assessment," filed Jan. 24, 2005. This related application is incorporated herein by reference and made a part of this application. If any conflict arises between the disclosure of the invention in this utility application and that in the related provisional application, the disclosure in this utility application shall govern. Moreover, any and all U. S. patents, U. S. patent applications, and other documents, hard copy or electronic, cited or referred to in this application are incorporated herein by reference and made a part of this application.

BACKGROUND OF THE INVENTION

1. Field of the Invention

This invention relates to the prevention and treatment of dental caries, including risk assessment, activity level, intervention and materials for the measuring said risk. Advanced clinical treatment procedures, methods and materials are presented and claimed herein.

2. Background and Related Art

Dentistry is usually considered to involve the restoration of natural teeth as they become carious. Cosmetic dentistry is another concept and an option with regard to tooth whitening and in some cases, orthodontia. In the July/August 2003 Dental Practice Report, Spaeth, in an article entitled "Not your father's dentistry" quotes Dr. G. V. Black who said, in 1896, that someday dentists would be "engaged in practicing preventive, rather than reparative, dentistry".

These sentiments were echoed in 1997, when Dr. Harold Slavkin discussed biological solutions to oral health problems including biological approaches to restorative dentistry in the repair destroyed by infection from *Streptococcus mutans*. There have been some patents that dealt with the idea of bacterial causes of dental decay and other problems. For example, Miehl in U.S. Pat. No. 5,213,615 uses active agents; said active agents are applied to the teeth as a dental varnish, cement, and the like. In RE 31,815 Alfano teaches a method for detecting the presence of caries in the teeth by the use of light beams of certain wavelengths and comparing the ratio of intensities of the lights in a plurality of carious and non-carious lesions in the mouth.

The prior art mentioned above dealt with advanced ways and means of the detection of carious areas of a patient's mouth. In U.S. Pat. No. 5,738,113 Connelly is concerned with the control and reduction of dental caries in people who are at risk of dental caries. Connelly discusses a method that applies fluoride and antimicrobial agents but does not provide a complete system for caries management by risk assessment.

In US patent application 20050191247, Drake et al discloses antimicrobial rinses and products based on chlorhexidine, alcohol free, xylitol and raspberry flavoring. Another US patent application, 20050169852, to Roberge et al, discusses antimicrobial rinses all based on CPC, cetyl pyridium chloride.

US patent application 20050142074 to Pushpangadan et al is concerned with antimicrobial rinses based on herbs and herbal root extracts. US patent application number 20050100866 to Arnone et al shows an electronic DC probe used to determine if decay is in a tooth based on electric resistance.

In US patent application number 20050025720 Bailey shows a oral maintenance kit based on xylitol products with gum, candy, rinse, toothpaste and the like. US patent application number 20020114768 by Stoor et al discloses antimicrobial rinses based on essential oils.

U.S. Pat. No. 6,846,478 to Doyle et al discloses oral antimicrobial rinses based on chlorite ion. Applicants' invention utilizes the hypochlorite ion as an antibacterial agent in various embodiments, not the chlorite ion. Applicants' invention comprises various rinses as well as an important diagnostic component.

Dental caries recently has been considered as a complex, transmissible bacterial infection. There are multiple pathogenic, cariogenic, bacteria involved in the dental caries process. Dentistry has identified a couple of the specific bacterial pathogens, but many of the bacteria remain unidentified and not culturable in the laboratory. Consequently, this complex process is not completely understood. Current scientific research is focusing not so much on the specific bacterial pathogens, but on the cariogenic bacterial biofilm that causes the disease, and the activity potential of that biofilm.

In contrast to the previous inventions in the field, the current invention is looking for and detecting amounts and types of bacteria in the mouth. This invention includes a plurality of screening tests for the detection of *Mutans* streptococci and Lactobacilli in the patient's saliva and tooth surfaces.

In addition to the levels of bacterial biofilm and the activity and activity potential of the bacterial biofilm it is seen as a diagnostic measure of the patient's presence of and risk for caries activity in their mouth. In this invention, one screening test is concerned with biofilm level in the mouth is determined by finding and measuring adenosine triphosphate (ATP), the energy molecule of living cells to measure the bioluminescence and to then correlate the amount of ATP present to the amount of bacterial load in the mouth.

The bacterial load in the mouth can also be measured with a second screening test, the protein detection screen; however, all teeth (even healthy teeth) are covered with a protective protein layer, the pellicle. The protein level as a determinant of the amount of bacterial biofilm present must account for the average pellicle protein baseline reading. In this invention, the presence of bacteria at high risk levels can be determined by a simple swab test looking for protein presence on the tooth surface. With a simple swab and reagent that results in a color change, bacteria on the tooth surface can be identified at high levels. The second swab test comprises a disposable protein sampler and identifying swab that changes color change indicator after swabbing. There is a color scale included with this swab test that helps to determine protein levels which are a direct result of levels of bacteria in the patient's mouth. A preferred commercially available color changing protein swab is the Biotrace Pro-Tect® system. This is a product of Biotrace Limited, located in Bridgend, in the UK. Details of the protein swab test and procedures will be described as part of the Detailed Description of the invention that follows.

The activity potential of the bacterial biofilm can be determined with the ATP bioluminescence. By taking a biofilm baseline reading of the ATP, then having the patient rinse with a specific concentration of a sugar in water solution for a specific time, then waiting a specific period of time and retesting. In a preferred embodiment, the sugar used is selected from the group consisting of sucrose and glucose, and the time period for retesting ranges from between 10 seconds and 10 minutes. The concentration of the sugar rinse used for this swab test is 0.1-40% by weight. Retesting for a second ATP level will provide a direct, calibrated, measure of the biofilm metabolic activity potential from which diagnostic decisions can be determined.

Yet another swab test that is part of this invention involves a rapid culture test for the detection of *Mutans* streptococci and Lactobacilli from the patient's tooth surface wherein the swab is removed from a sterile package; rubbed on a tooth surface, transferred to an agar tube selective for *Mutans streptococcus*, incubated at body temperature (37 degrees C.) for 3-24 hours, and read for the number of colony forming units of *Mutans* streptococci and Lactobacilli.

The system of the instant invention includes a diagnostic testing component, a diagnostic survey questionnaire, and a plurality of antimicrobial treatment components. Caries risk assessment and treatment procedures are now the standard of care in California and it may become standard in other locations. Details on the components, materials and methods of the invention will be detailed shortly.

SUMMARY OF THE INVENTION

This invention provides a complete turnkey system for caries risk assessment and treatment, including a protein test, an ATP test and a rapid bacterial culture test, and a plurality of rinses and educational and diagnostic materials. The system for the detection and treatment of the bacterial infection that causes dental caries in a patient comprises a disposable protein identifying swab with a color change indicator, a disposable ATP Bioluminescence sampler to swab areas of the patient's mouth, a bioluminescent light meter which measures the amount of ATP present in the patient's mouth, a rapid culture test for the detection of *Mutans* streptococci and Lactobacilli, a diagnostic testing component that includes a caries risk assessment questionnaire, a treatment component that includes a therapeutic oral rinse comprising at least two components, a daily treatment component selected from the group comprising an oral rinse and an oral spray to be used by the patient independently, and a patient diagnostic survey questionnaire, which is assessed by a dental professional and that, with a decision tree, pinpoints any oral bacterial infection that exists in the patient that causes dental caries.

A preferred ATP Bioluminescence sampler to swab areas of the patient's mouth of this invention is the UltraSnap™ swab made by the Hygenia Company. UltraSnap is a simple and effective means for sampling which has a self-contained ATP device to measure ATP levels and the bacterial levels in a patient's mouth.

BRIEF DESCRIPTION OF THE FIGURES

FIG. 1 depicts the Caries Risk Assessment Form of this invention

FIG. 4A shows the swab being rubbed on a tooth surface and FIG. 4 shows the swab placed in the protective swab tube after swabbing has been done

DEFINITIONS USED IN THIS INVENTION

Figure 2:
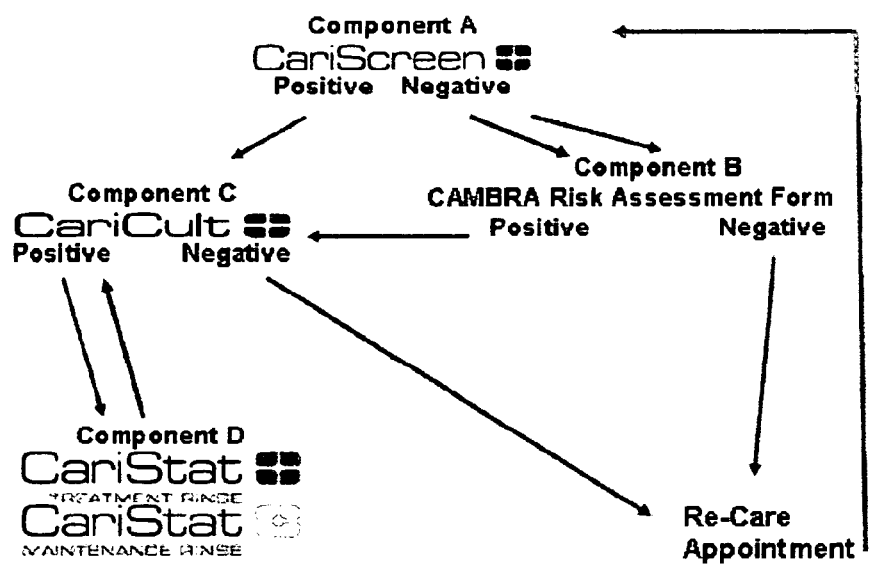
FIG. 2 depicts the CAMBRA Decision Tree of this invention

For purposes of this invention, a dental professional can be a dentist, a dental hygienist or a certified dental assistant.

In this invention, caries and periodontal disease are the oral health conditions that are being treated and improved by the system, methods and kit of the present invention

DETAILED DESCRIPTION OF PREFERRED EMBODIMENTS

The present invention deals with a biological approach to treatment of a patient's oral health problems. A large part of this approach involves the measurement of the types and amounts of bacteria present in the patient's mouth. It is known that while numerous different bacteria play major roles in dental caries and periodontal disease and many have yet to be identified. Two specific bacteria have been consistently identified with dental caries risk. These bacteria are *Mutans* streptococci and Lactobacilli. Measurement of these bacteria in a patient's saliva enables the dental professional to treat the patient with a goal of long-term dental health. The instant invention provides a plurality screening tests, diagnostic guidelines, professional assessment forms, oral rinses and a daily treatment program to ensure and preserve the patient's long term oral health.

With reference to FIG. 1, a Caries Risk Assessment Form (CRAF) is completed by a dentist, or otherwise qualified dental professional while a patient visits a dental office. The patient is an adult or a child over the age of six years. Caries risk assessment can be performed on children under the age of six years, with additional considerations.

In general, patients with high risk of caries include: those with recurrent or residual decay, as shown by their treatment history; patients who are about to receive orthodontic care (as it is known that orthodontic appliances and/or brackets are natural sites for colonization of *Streptococcus Mutans*; patients with crown and bridge restorations; patients with limited salivary flow (xerostomia) due to systemic medications such as anti-hypertensive medicaments, anti-depressants, tranquilizers, antihistamines, and other drugs known to reduce saliva flow. Also factors are certain systemic diseases such as Sjogren's Syndrome, scleroderma, lupus, rheumatoid arthritis, or with neurological conditions such as Parkinson's Disease. Also at high risk are new patients exhibiting poor oral hygiene, poor dental knowledge and/or poor compliance with following instructions; and patients under periodontal care with exposed root surfaces. Age is a factor in that patients at peak periods for decay are often in their early teens, 20's and over 55 years of age.

The present invention uses the CRAF of FIG. 1 to assess a patient's risk level. The CRAF has four columns labeled 1, 2, 3 and 4. The CRAF can be a paper document and/or part of the patient's computerized dental record. As seen in FIG. 1, the CRAF column 1 lists seven factor categories in rows and a plurality of items under each category and three columns that classify the factors into rankings of HIGH, MODERATE, and LOW for each. The factors listed in column 1 of the CRAF are selected from the group consisting of local factors, dental conditions, medical history, dietary habits, environmental issues, protective factors and laboratory tests.

The first category of risk factors in column 1 or the CRAF is local factors. The local factors are the presence of dental plaque and/or calculus. The dental professional completing the form would indicate the presence of plaque and/or calculus by indicating if these factors are present or not present by using the columns headed high, moderate, and low.

The next category of column 1 is labeled 'dental conditions' and lists "visible cavitation", "cavity in last three years", "inadequate saliva flow" exposed roots", "deep pits/fissures", "radiographic lesions" and "white spot lesions", and "appliances present"

The next category in column 1 is MEDICAL HISTORY. Factors that indicate a high caries risk in this category are listed in column 2 and include "Sjogren's syndrome", "hyposalivary meds", and "radiation therapy". The next category in column 1 includes DIETARY HISTORY and indicates in column 2 that a high risk is present for ">3 snacks between meals" and "regular (sugar-sweetened) soda". The fifth category assigns a high risk factor to the use of "recreational drugs" under the category ENVIRONMENTAL. The sixth category of column 1 is PROTECTIVE FACTORS. In this category, high risk is assessed in column 2 when there is no "fluoridated water", no "fluoridated toothpaste use", and "inadequate saliva flow." The seventh category, LABORATORY TESTS in column 2, indicates the recommendation of both "saliva flow" and "Caricult rapid culture tests" for patients at high risk.

Column 2 of the CRAF of FIG. 1 represents those patients at relatively high risk of caries. Typical responses that will fall into the high risk category are those patients having recent cavitation, inadequate saliva flow, dental appliances present, and who have at least one of the listed medical conditions, eat sugary snacks and/or beverages, use recreational drugs, and are low on protective factors such as fluoridated water and/or toothpaste.

Column 3 of the CRAF of FIG. 1 contains the responses that categorize a patient at moderate risk. These responses include localized plaque/calculus, and "yes" responses in the areas under the DENTAL CONDITIONS of "exposed roots", "deep pits/fissures", "radiographic lesions" and "white spot lesions".

Regarding the risk factors under "Dietary Habits", moderate risk caries patients snack between meals 1-3 times and have infrequent use of regular soda. Patients at moderate caries risk likely use no fluoride mouth rinse, no xylitol gum or mints, no chlorhexidene rinse, and no povidone Iodine rinse. Depending upon the moderate risk patient's ATP bioluminescence Cariscreen score, they may be indicated for the Caricult rapid culture test.

Patients at low risk are addressed in Column 4 of the CRAF of FIG. 1. They have minimal or no plaque/calculus, no positive responses in the entire category of DENTAL CONDITIONS, no positive responses in the entire category of MEDICAL HISTORY, infrequent snacking between meals, no regular soda, no use of recreational drugs, and all positive responses in the PROTECTIVE FACTORS category.

Prior published studies of patients show that between 30% and 40% have Streptococcus mutans infections in their oral cavities at levels above 250,000 colony forming units per milliliter (cfu/ml). The level of 250,000 cfu/ml is an internationally recognized standard of caries risk (see I. Zickert et al, "Effect of Caries Preventive Measures in Children Highly Infected with the Bacterium Streptococcus mutans, in J. Oral Biol., 1982, pp. 861-868).

Typically, 10% of patients are high risk and 20% are medium risk as measured by the levels of Streptococcus mutans in their oral cavity. There are certain objective measures of Streptococcus mutans levels which are available to determine whether a patient is at high or medium risk of caries. Prior art testing procedures are available in the marketplace, including CARIESCREEN by APO Diagnostics Inc. or the CRT saliva test manufactured by Ivoclar-Vivadent. Categorization of patients into low risk, medium risk and high risk is essential to provide the optimal frequency of dental treatments to prevent future dental caries. This is a significant factor as those at medium risk and high risk that, if left untreated, will be at greater risk of developing symptoms (cavities) of the disease.

In addition to the necessity of objectively measuring Streptococcus mutans (MS) levels in the oral cavity, the CRAF of this invention provides insight into the dental and medical history of the patient, the oral hygiene habits of the patient, the age of the patient, and the type of medications the patient is taking. It is known that the presence of Streptococcus mutans is essential for the development of dental caries. It is also known that certain risk factors operate in determining caries risk.

While low risk is indicated by having less than about 250,000 cfu/ml Streptococcus mutans, one could distinguish further between a lower risk group having 100,000 to 250,000 cfu and a very low risk group at less than 100,000 cfu. Objective measurements of levels of Streptococcus mutans can be used as an indicator of an individual's likelihood of developing dental caries in the future as well as control of existing dental caries.

The relationships between bacterial counts in the oral cavity and the development of dental decay and future prognosis in a patient are still being investigated. In fact, some studies are suggesting that the cut-off for high risk be lowered to 1000,000 cfu for MS. The system of the present invention are advantageous in that they provide both the dental treatment provider with a tool to control and reduce the incidence of dental caries and the patient do proactively play an important, preventative role in his or her dental and periodontal health. The system is particularly beneficial for reducing patient risk of dental caries in the population of patients with good nutritional habits and good habits of dental hygiene.

Patients in a high risk group could be treated and monitored with the system and methods of the present invention to see if their risk grouping drops to medium risk. Similarly those in the medium risk could be monitored to see if they could move to a low risk group. The treatment guidelines for the new risk group would then apply for the patient. If a patient did not drop into a lower risk group then the dental treatment provider would know to continue with the current treatment for that risk group. This may also be a signal to the dentist that other factors, which were not at first appreciated or realized, may be at work. In the latter situation, the treatment methods of the present invention may act as an indictor of the overall oral health of the patient.

Each of the CRAF responses is assessed by the patient's dentist to determine the caries risk status of each individual patient. It is especially important to identify individuals with high Streptococcus mutans levels in their oral cavities. To measure the actual bacteria count, the dental professional uses a method of assessing the level and type of oral bacteria to determine the prognosis for the development of caries in a patient which includes the steps of
  a) Swabbing an area of the patient's mouth with a disposable tool;
  b) Performing a rapid culture test for the detection of *Mutans streptococcus* and Lactobacilli;
  c) Using a bioluminescent light meter to interpret the test results;
  d) Diagnosing the likelihood for caries risk on the tested area of the mouth;
  e) Combining these test results with the answers to patient survey forms, and using the decision tree shown in FIGS. 1 and 2 and examination by dental professionals to produce a individualized caries risk assessment profile for the patient. The caries risk profile will then help the dentist to prescribe a series of specific treatments for said patient. The rapid culture test uses an agar medium that favors *Mutans* streptococci, has a color change indicator, and is incubated at human body temperature, 37 C for a period of 3-24 hours before being read for the number of colony forming units.

The patient's risk assessment profile is done using the completed CRAF of FIG. 1, when combined with the decision tree of FIG. 2, pinpoints any oral bacterial infection that exists in the patient that causes dental caries.

To do this, the dental professional starts with component A of FIG. 2, the initial swabbing of the oral cavity followed by the performance of a rapid culture test. The swab used is shown and described in FIGS. 4 and 4A and is more fully described below. A bioluminescent light meter (shown in FIGS. 7 and 8) is used to interpret the results of the ATP swab tests. The results of A can be either positive or negative; if they are negative the next point on the decision tree is component B, the caries risk assessment form, the CRAF of FIG. 1. The patient completes the CRAF; if the results of this are negative for caries risk, the patient is scheduled for a recall appointment. If the results of component B are positive, the patient moves on to step C which is a rapid culture test for the detection of *Mutans* streptococci from the patient's saliva.

Step C is another decision point on FIG. 2; if the rapid culture test produces negative results, the patient is scheduled for a recall appointment. If the culture test is positive, the patient is now on step D of the decision tree. Step D is the application of a therapeutic rinse for a specified period of time determined by the dentist, usually from 1-3 weeks. After this time, the patient is placed on a daily maintenance rinse, to be used independently after completing the therapeutic rinse.

After repeated use of the daily maintenance (fo a usual time period of about 3 weeks, the is retested at the dental office and the rapid culture test of step C to assess the effectiveness of the treatment and patient behavioral modification. This procedure is repeated until Step C gives a negative result for the detection of *Mutans* streptococci.

This invention includes at least two rinses. The rinses include a treatment component that includes a short term therapeutic oral rinse and a long term maintenance treatment component that comprises a long term maintenance rinse and an oral spray to be used by the patient independently.

The short term therapeutic rinse of this invention is a two component product. The first of the two components of the short term therapeutic rinse is comprises at least one sugar-free taste enhancing agent, at least one solvent, at least one carrier, at least one preservative and a flavoring. More specifically, the first of the two components of the therapeutic rinse comprises xylitol as the sweetener, water as the carrier, Poloxamer 407 as the surfactant, flavor enhancers selected from the group consisting of menthol, peppermint, cranberry, cinnamon, citrus, mint oil and lemon, sodium benzoate as the preservative, and sodium fluoride for anticavity protection and remineralization.

Poloxamers are a non-ionic surfactants which are polyoxyethylene polyxypropylene block copolymers. In the present invention, the poloxamer 407 is bought from Voigt Global Distribution of Kansas City, Mo.

The second of the two components of the short term therapeutic rinse comprises at least one antimicrobial agent, a carrier, and sufficient pH adjusters to bring the pH to a basic value higher than 7.0. More specifically, the second of the two components of the therapeutic rinse comprises sodium hypochlorite as the antimicrobial agent, water as the carrier, and sodium hydroxide as the pH adjuster.

Another rinse of this invention is the long term maintenance rinse. It is used by the patient independently and comprises at least one antimicrobial agent, a solvent, at least one flavoring, a preservative, at least one pH adjuster, and at least one remineralization agent. The remineralization agent is selected from the group consisting of fluoride, calcium and phosphate ions in the form of water soluble salts.

More specifically, a preferred long term maintenance rinse flavoring is xylitol, the solvent is water, the antimicrobial agents are selected from the group consisting of polyphenols of white tea extract and anthocyanidins of cranberry extract, the preservative is sodium benzoate, the remineralization agent is sodium fluoride, and the pH adjuster is sodium bicarbonate. The pH adjuster is present to insure that the pH of the long term maintenance rinse is higher than 7

The long term maintenance treatment of this invention may also include a spray that is used for antimicrobial treatment, acid buffering, and remineralization. A preferred oral spray comprises the flavoring of xylitol, the solvent is water, the antimicrobial agents are selected from the group consisting of polyphenols of white tea extract and anthocyanidins of cranberry extract, the preservative is sodium benzoate, the remineralization agents are calcium and phosphate ions, and the pH adjuster is sodium bicarbonate.

Additional products included in the system of this invention include oral chewing substances made of natural leaf products selected from the group consisting of mint leaves, tea leaves, herbal leaves, tobacco leaves, the flavoring is xylitol, the solvent is water, the antimicrobial agents are selected from the group consisting of polyphenols of white tea extract and anthocyanidins of cranberry extract, the preservative is sodium benzoate, the remineralization agent is selected from the group consisting of calcium and phosphate ions, and the pH adjuster is sodium bicarbonate.

Figure 3:
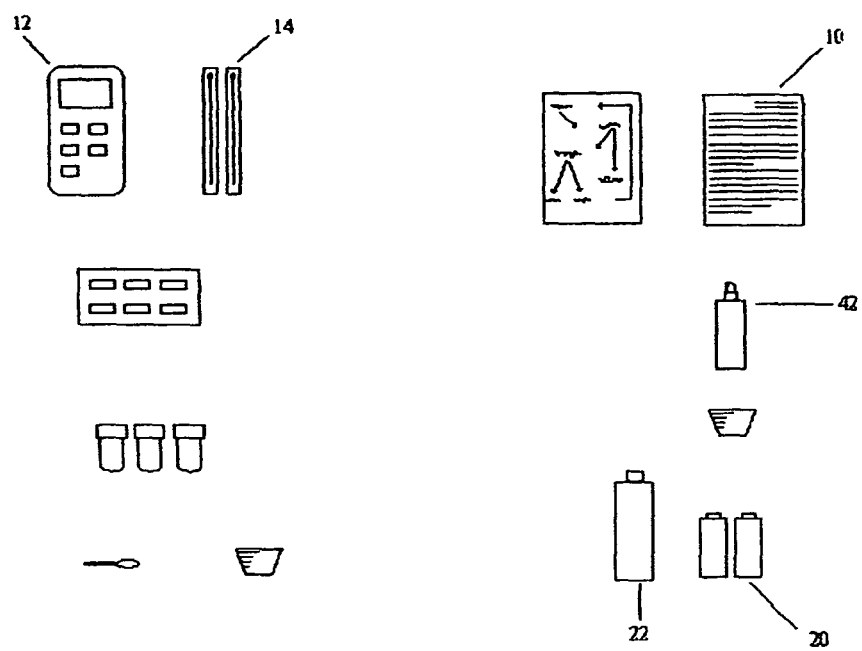
FIG. 3 depicts the components of a kit of this invention

The instant invention includes a kit for patients use in conjunction with professional dental treatment in the control of oral bacterial infection to prevent the occurrence of dental decay in patients. As depicted in FIG. 3, the kit includes
  i) a first rinse that is a two-part short term therapeutic rinse 20 that reduces *Mutans* streptococci and Lactobacilli levels and whose components are listed supra.
  ii) a second long term maintenance rinse 22
  iii) an oral spray that is packaged in a plastic spray bottle and that comprises a flavoring, a solvent, an antimicrobial agent, a preservative, a remineralization agent, and a ph adjuster.

The rinses of this invention are a large part of the uniqueness and utility of the present invention. The two-component short term therapeutic rinse can be made using the following formula

| Component one: CAMBRA CariStat ™ Treatment ORAL RINSE | |
| --- | --- |
| Component Rinse A | % Wt |
| Water | 72.70 |
| Xylitol | 22.0 |
| Mint Oil | 1.0 |
| Sodium Benzoate | 2.0 |
| Poloxamer 407 | 1.25 |
| Menthol | 1.0 |
| Sodium Fluoride | 0.05 |
| Total Rinse | 100 |

In the above formulation, xylitol is a sweetener, sodium benzoate is a preservative, sodium fluoride is a decay-preventive and remineralization agent, sodium bicarbonate is a pH buffer, menthol is a flavoring and water is the solvent.

| Component two: Component Rinse B | |
| --- | --- |
| 6% Sodium Hypochlorite Solution | 2.84 gal |
| Water | 42.6 gal |
| 18% Sodium Hydroxide Solution, added to achieve a solution pH of 11.9 | |

In the above formulation, sodium hypochlorite is the antimicrobial agent, sodium hydroxide is present to keep the pH of the formula at or above a pH value of 7 and water is the solvent.

The CariStat™ maintenance rinse with Fluoride has the following formula Single Component Long Term Maintenance Rinse

| | Weight (lbs) | Weight percent |
| --- | --- | --- |
| Xylitol | 114.4 | 25% |
| Water 40 gal | 333.9 | 72.95% |
| Sodium Benzoate | 9.15 | 2% |
| Sodium Fluoride | .228 | .05% |
| Sodium Bicarbonate | | to pH of 7+ |
| Natural Flavoring (lemon) | | ¼ cup |
| Color (Red, Yellow) | | |

The ingredients listed above are present as a sweetener (xylitol), a preservative (sodium benzoate), anti-cavity/remineralization agent (sodium fluoride), pH buffer (sodium bicarbonate), solvent (water) and flavor (lemon) and color (red).

EXPERIMENTAL DATA

Figure 4:
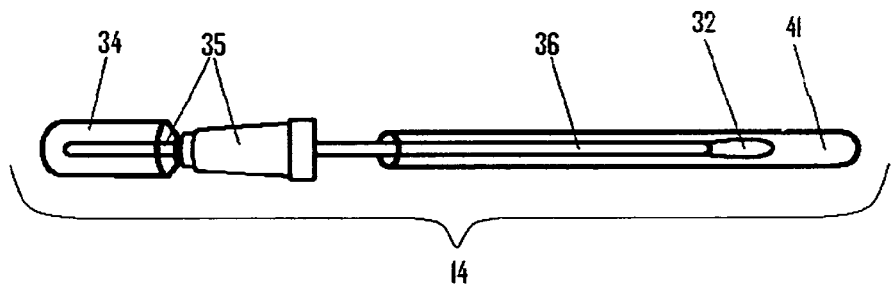
FIGS. 4 and 4*a* shows the "SNAP-SWAB" of this invention.

All patients who are treated for the prevention and treatment of dental caries, including risk assessment, activity level, and intervention begin their treatment by being swabbed and categorized for caries risk based on the following procedure:

The CariScreen™ Swab sampling device shown in FIG. 4 is a self-contained ATP device for use with the CariScreen Meter used for Caries Susceptibility Testing. This system is used as a screening test for the presence of high dental caries risk. The CariScreen Meter in conjunction with the CariScreen Swab measures adenosine tri-phosphate (ATP), the universal energy molecule found in all animal, plant, bacterial, yeast, and mold cells.

When collecting a sample, the dental professional must make sure to use aseptic techniques; care must be taken to not touch the swab or the inside of the sampling device with fingers. The patient's mouth should be at rest, which in general terms means no mechanical activity, brushing, flossing, swishing, coughing, chewing, eating and the like for a period of 15-30 minutes prior to the test.

Figure 4A:
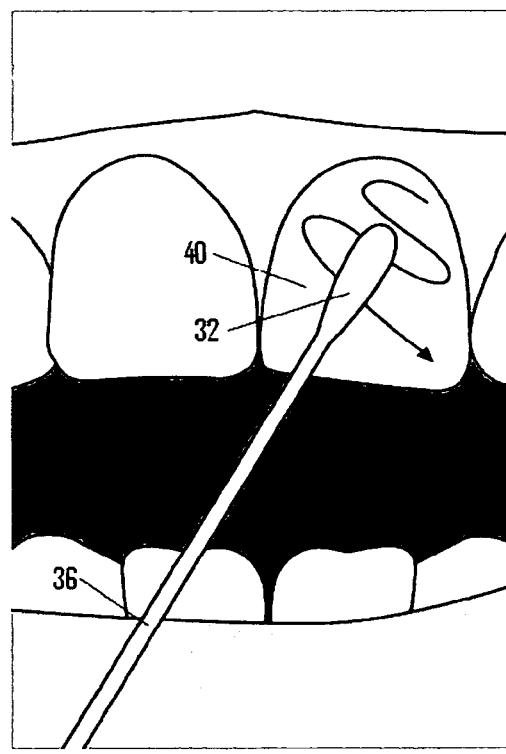

The first step of swab sampling is to remove the swab which ends in a tip 32 from the swab tube 41. The swab tip 32 is rubbed on a tooth surface 40 as depicted in FIG. 4A. After swabbing, the swab 32 is put back into the swab tube 41.

Figure 9:
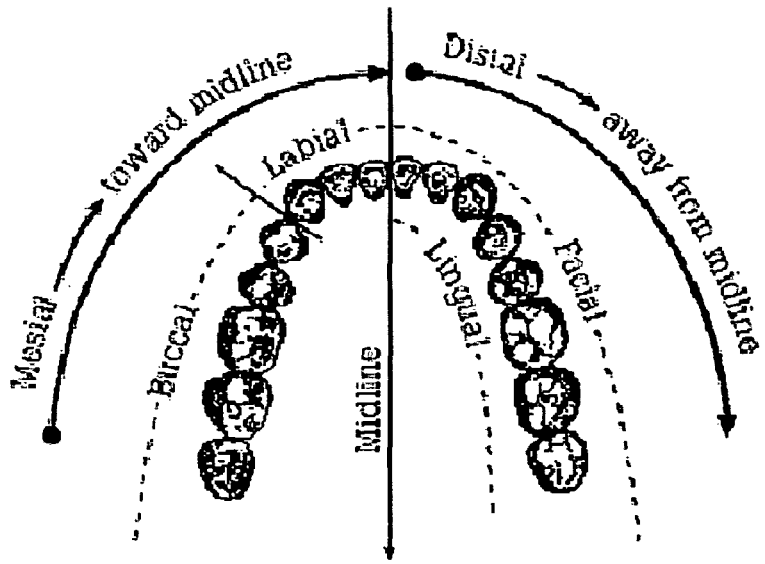
FIG. 9 is a view of a patient's dentition

Condensation may be visible on the inside of the swab tube, which is normal. The buccal surface of a maxillary molar in the gingival third without touching the gingiva is swabbed carefully with the swab tip. The swab tip is moved across the tooth surface three times from mesial to distal. Use the maxillary right first molar if it is present; if not present select the second molar or premolar to swab instead. Using the same swab, carefully swab a maxillary incisor in the gingival third with the same protocol: swab three times across the surface from mesial to distal being sure not to contact the gingiva. Use the maxillary right central incisor-if it is present; if not present select another incisor and swab it with the same protocol. A patient's dentition is shown in FIG. 9, which diagrams a mouth. The mesial, distal, buccal, lingual, and facial areas of the mouth are shown along with some further explanatory notes.

After swabbing the desired test area, place swab 32 back in swab tube 41. The sample can be left for up to 4 hours on the cotton ball-end of the swab before activating the device, however once activated the sample must be read in the CariScreen Meter within 60 seconds.

Figure 5:
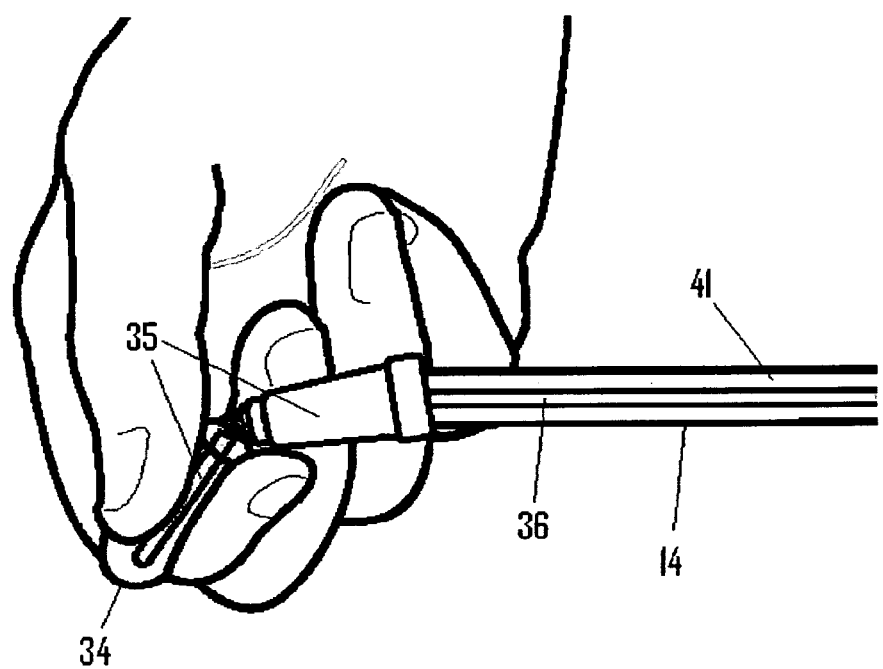
FIG. 5 shows a user whose hand is breaking the "SNAP-VALVE" at the top of the swab by bending the bulb of the swab tube

ATP is brought into contact with a sample of the swab tip 32 when a user snaps the snap valve 35 between the bulb 34 and the swab shaft 36 as seen in FIG. 5. The unique liquid-stable luciferase/luciferin reagent contained in the bulb 34 of CariScreen Swab sampling device 14, light is emitted in direct proportion to the amount of ATP present.

Figure 6:
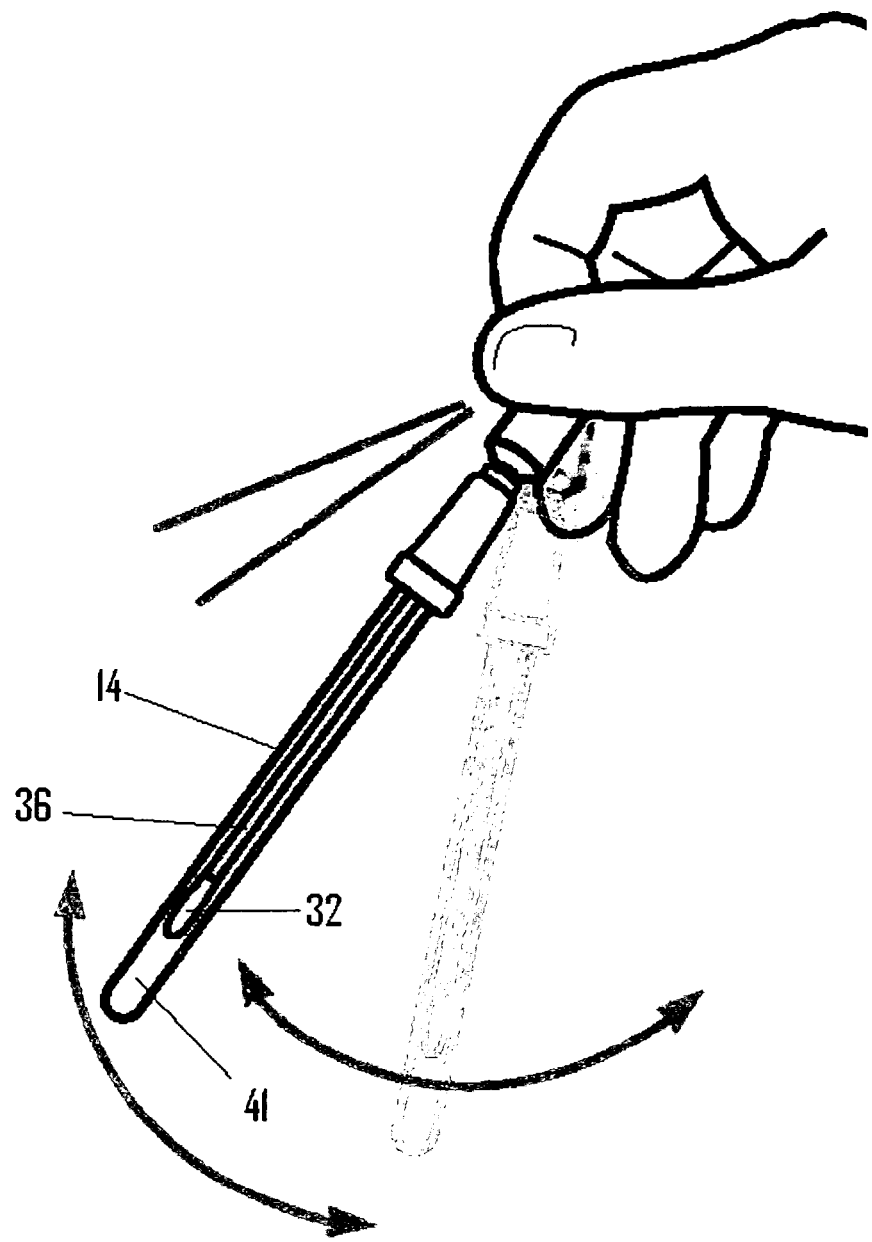
FIG. 6 shows a user shaking the swab

FIG. 5 depicts the activation of the device. It is activated by holding the swab tube 41 firmly, and using the thumb and forefinger to break the snap valve 35 by bending the bulb 34 forward and backward. Squeeze the bulb twice, expelling all liquid down the swab shaft 36. Bathe the swab bud in liquid by gently shaking for 5-10 seconds as shown in FIG. 6.

Figure 7:
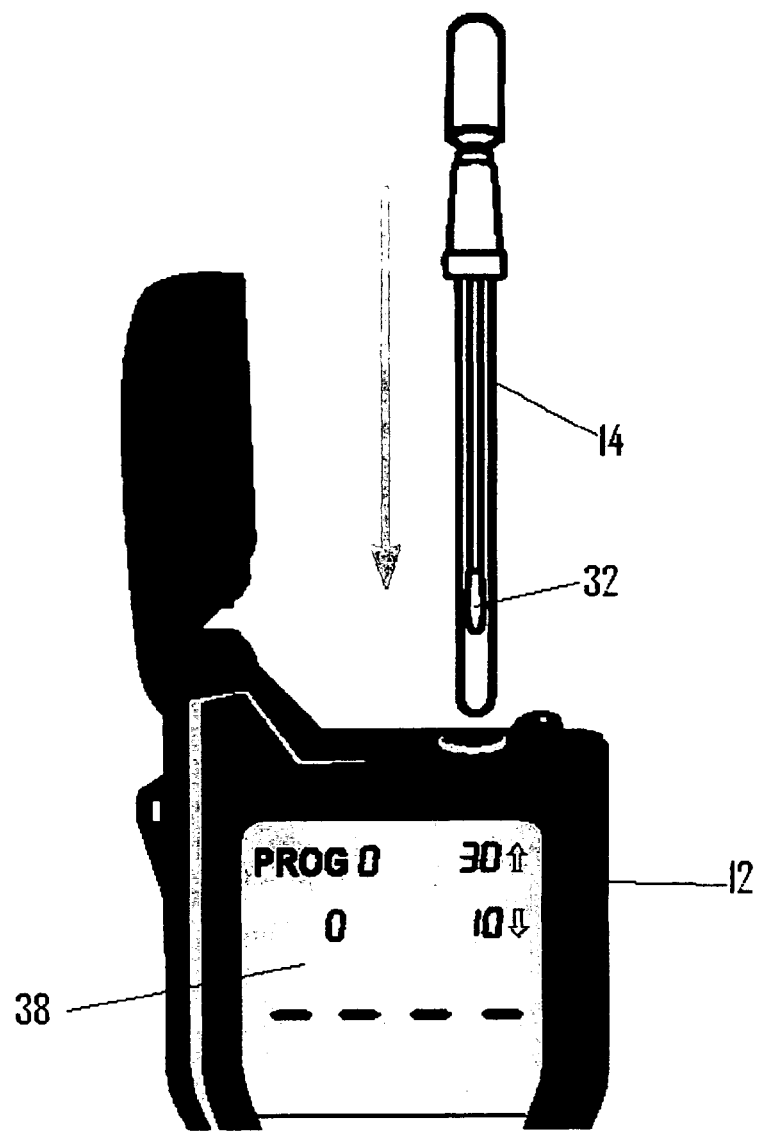
FIG. 7 shows the swab being placed in the ATP bioluminescence light meter
Figure 8:
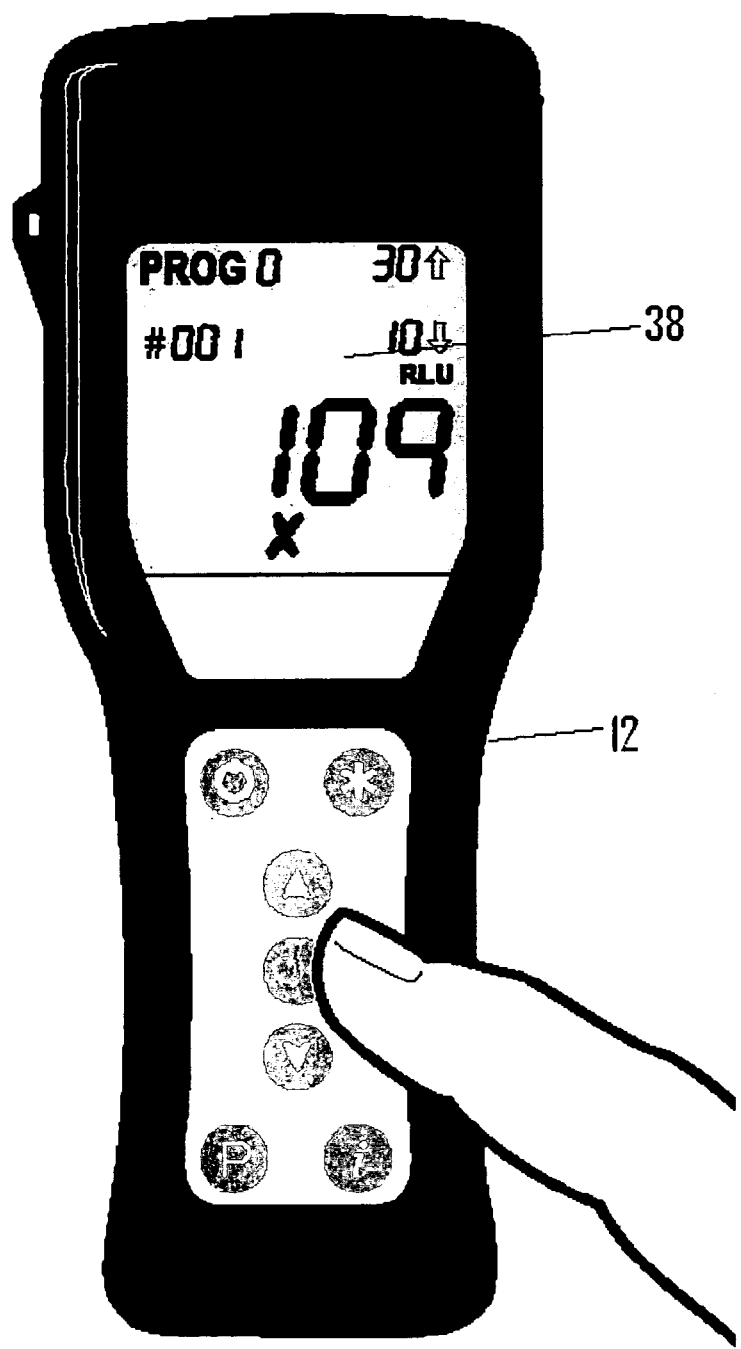
FIG. 8 shows the ATP screen that shows the bioluminescence light meter test results for the swab placed therein

FIGS. 7 and 8 display the reading and interpretation of the results of the swab test. The swab 14 is inserted into a ATP bioluminescence light meter such as the CariScreen Swab bioluminescent light meter 12. The lid is closed and read the results by pressing "OK". A 15-second sequence will then commence. Results should be read within one minute of activation of the ATP light meter 12.

The reading will appear on the screen 38 of the ATP light meter 12 as a number of RLUs (1-9999). This number is recorded for the patient on the CRAF form 10 Values correspond to level of risk as follows:
 0-1500=low risk
 1501-3500=moderate risk
 3501-9999=high risk
 There will also be an icon in the lower portion of the screen 12 indicating low, moderate, or high risk. The ATP bioluminescence instrument manual will contain further user information and details.

Cases:

Case 1) Patient 1 was a 48-year-old Caucasian male who does blue collar work. He presented for oral examination and was examined and tested for caries risk assessment. Upon screening, an ATP Bioluminescence swab 14 was swabbed over the buccal surface of the maxillary first molar in the gingival third three times. After this was done, also swabbed on the labial surface of the maxillary central incisor in the gingival third three times, after which the swab was placed into the ATP Bioluminescence light meter 12. The reading in relative light units (RLU) after 15 seconds was 4242 indicating this patient was potentially high risk for dental caries. As a next step in the system, the patient was both cultured with a rapid culture for *Mutans* Streptococci and surveyed with the CRAF form 10 of FIG. 1. The results of the culture demonstrated CFU's colony forming units greater than $10^5$, indicating high risk. The completed CRAF form 10 also demonstrated a high risk for caries.

A diagnosis of the bacterial infection that is responsible for dental caries was confirmed. The patient was treated with the short term therapeutic two-component oral rinse 20 once per day for two weeks. This was followed by treatment with the long term maintenance oral rinse 22 on an ongoing basis. The patient was subsequently cultured at the end of one month and the bacterial rapid culture demonstrated fewer than $10^5$ colony forming units of *Mutans* streptococci, indicating that the infection had been controlled and the patient was now at low risk for the bacterial infection responsible for dental caries. The patient was placed back into a normal re-care appointment schedule for regular dental check-ups, which will include routine ATP Bioluminescence swab 14 screening.

2) Patient 2 was a 56-year-old Caucasian female patient who is a white collar professional. She presented for a routine dental re-care appointment and caries risk assessment. Upon screening with the ATP Bioluminescence swab 14, which was swabbed over the buccal surface of the maxillary first molar in the gingival third three times, and then also swabbed on the labial surface of the maxillary central incisor in the gingival third three times. The swab 14 was then placed into the ATP Bioluminescence light meter 12. The reading in RLU's after 15 seconds was 321 indicating this patient was low risk for dental caries. As a next step in the system, the patient was surveyed with the CRAF Risk Assessment form 10. The results of the questionnaire indicated the patient was low risk for dental caries. A diagnosis was confirmed that the patient was low risk for the bacterial infection responsible for dental caries, and the patient was placed back into the normal re-care scheduling for dental check-ups.

SCOPE OF THE INVENTION

The above presents a description of the best mode contemplated of carrying out the present invention, and of the manner and process of using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A method of testing the level of caries causing bacteria in a sample from a tooth of an individual patient, including the steps of
   (a) providing an assembly of a tube, a sampling device that holds a manually releasable liquid reagent, and a swab for collecting from a surface of said tooth the sample to be tested, said swab extending into the tube and being removable from the tube and replaceable therein after collecting said sample,
   (b) removing the swab from the tube and collecting said sample from a surface of said tooth by rubbing said surface with the swab,
   (c) replacing in the tube the swab with the collected sample thereon and manually releasing the reagent so said reagent contacts the sample on the swab while still within the tube,
   (d) inserting the tube with the swab and collected sample thereon into a light meter that provides a reading corresponding to caries causing bacteria levels in the sample on the swab, and
   (e) taking the reading with the light meter, said reading corresponding to the level of caries causing bacteria in the sample.

2. The method of claim 1 where the patient answers questions that assist in assessing risk of caries and combining the test results from step (e) with the answers and an examination by a dental professional producing an individualized risk assessment profile of the patient to aid the dental professional in prescribing a specific treatment.

3. The method of claim 1 where the reading is taken within 60 seconds after the reagent contacts the swab.

4. The method of claim 1 where the patient's mouth is at rest from 15 to 30 minutes prior to testing.

5. The method of claim 1 where after releasing the reagent the tube is shaken from 5 to 10 seconds.

6. A method of testing the level of caries causing bacteria in a sample from a tooth of an individual patient, including the steps of
   (a) providing an assembly of a tube, a sampling device that holds a manually releasable liquid reagent, and a swab for collecting from a surface of said tooth the sample to be tested, said swab extending into the tube and being removable from the tube and replaceable therein after collecting said sample,
   (b) removing the swab from the tube and collecting said sample from a surface of said tooth by rubbing said surface with the swab,
   (c) replacing in the tube the swab with the collected sample thereon and manually releasing the reagent so said reagent contacts the sample on the swab while still within the tube and shaking the tube,
   (d) inserting the shaken tube with the swab and collected sample thereon into a light meter that provides a reading corresponding to caries causing bacteria levels in the sample on the swab, and
   (e) taking the reading with the light meter within 60 seconds after the reagent contacts the swab, said reading corresponding to the level of caries causing bacteria in the sample,
   the patient's mouth being at rest from 15 to 30 minutes prior to testing.

7. The method of claim 6 where the patient answers questions that assist in assessing risk of caries and combining the test results from step (e) with the answers and an examination by a dental professional producing an individualized risk assessment profile of the patient to aid the dental professional in prescribing a specific treatment.

* * * * *